(12) United States Patent
Bernard et al.

(10) Patent No.: US 6,908,441 B1
(45) Date of Patent: Jun. 21, 2005

(54) URINE COLLECTION DEVICE

(76) Inventors: Clifford Bernard, 13974 Simshaw Ave., Sylmar, CA (US) 91342; Shelia Bernard, 13974 Simshaw Ave., Sylmar, CA (US) 91342

( * ) Notice: Subject to any disclaimer, the term of this patent is extended or adjusted under 35 U.S.C. 154(b) by 196 days.

(21) Appl. No.: 10/259,922

(22) Filed: Sep. 27, 2002

(51) Int. Cl.$^7$ ............................ A61B 5/00; B65D 81/00
(52) U.S. Cl. ........................................... 600/574
(58) Field of Search ................................ 600/580, 573, 600/574, 576; 604/329, 317, 318, 326, 331, 604/327, 347, 355; 4/144.2, 458, 144.3, 144.4

(56) References Cited

U.S. PATENT DOCUMENTS

| 622,631 | A | | 4/1899 | Orbeton | |
|---|---|---|---|---|---|
| 3,750,647 | A | | 8/1973 | Gleason et al. | |
| 3,832,738 | A | | 9/1974 | Kliemann | |
| 4,106,490 | A | * | 8/1978 | Spilman et al. | 600/574 |
| 4,331,162 | A | * | 5/1982 | Kuntz et al. | 600/574 |
| 4,753,249 | A | * | 6/1988 | Muller | 600/584 |
| 4,790,837 | A | | 12/1988 | Gross et al. | |
| 5,333,330 | A | * | 8/1994 | Murtagh | 4/144.3 |
| D370,975 | S | | 6/1996 | Mohr | |
| 5,711,310 | A | | 1/1998 | Vinayagamoorthy et al. | |
| 6,299,606 | B1 | * | 10/2001 | Young | 604/329 |
| 2002/0193760 | A1 | * | 12/2002 | Thompson | 604/318 |
| 2003/0140409 | A1 | * | 7/2003 | Johnson | 4/458 |
| 2003/0149408 | A1 | * | 8/2003 | Levinson | 604/329 |

* cited by examiner

*Primary Examiner*—Max F. Hindenburg
*Assistant Examiner*—Brian Szmal

(57) ABSTRACT

A urine collection device for facilitating collection of urine samples from a user. The urine collection device includes a funnel member having a bowl portion and a stem portion. The bowl portion has perimeter wall defining a cavity. The cavity of the bowl portion has an open top whereby the open top of the cavity is designed for permitting urine to enter the cavity of the bowl portion. The stem portion has a bore. The bore is in fluid communication with the cavity of the bowl portion whereby the bore of the stem portion is designed for permitting urine collected in the bowl portion to pass through the stem portion. A collection member is selectively coupled to the stem portion of the funnel member opposite the bowl portion for collecting and storing urine when the urine has passed through the bore of the stem portion of the funnel member.

13 Claims, 3 Drawing Sheets

URINE COLLECTION DEVICE

BACKGROUND OF THE INVENTION

1. Field of the Invention

The present invention relates to apparatus for collecting urine samples and more particularly pertains to a new urine collection device for facilitating collection of urine samples from a user.

2. Description of the Prior Art

The use of apparatus for collecting urine samples is known in the prior art. U.S. Pat. No. 5,711,310 describes a system for collecting a mid-stream urine sample. Another type of apparatus for collecting urine samples is U.S. Pat. No. 3,832,738 having a funnel shaped member connected to a container for collecting urine mid-stream. U.S. Pat. No. 622,631 has a tapering tubular body to pressed against the body to aid in urinating into a receptacle. U.S. Pat. No. 3,750,647 has an apparatus of obtaining a urine sample from a female. U.S. Pat. No. 4,790,837 has a urine meter for measuring the amount urine expelled from the body of the user. U.S. Patent No. des. 370,975 shows a urine relief tube.

While these devices fulfill their respective, particular objectives and requirements, the need remains for a device that has certain improved features to provide cushion for the user while using.

SUMMARY OF THE INVENTION

The present invention meets the needs presented above by providing a forward pad member and a rearward pad member to cushion the user from the bowl portion when the bowl portion is positioned for use.

Still yet another object of the present invention is to provide a new urine collection device that facilitates collection of urine by a user.

Even still another object of the present invention is to provide a new urine collection device that allows flexibility in positioning to make collection of urine more comfortable.

To this end, the present invention generally comprises a funnel member having a bowl portion and a stem portion. The bowl portion has perimeter wall defining a cavity. The cavity of the bowl portion has an open top whereby the open top of the cavity is designed for permitting urine to enter the cavity of the bowl portion. The stem portion has a bore. The bore is in fluid communication with the cavity of the bowl portion whereby the bore of the stem portion is designed for permitting urine collected in the bowl portion to pass through the stem portion. A collection member is selectively coupled to the stem portion of the funnel member opposite the bowl portion. The collection member has a peripheral wall defining an interior space. The interior space of the collection member is in fluid communication with the bore of the stem portion of the funnel member. The interior space of the collection member is designed for collecting and storing urine when the urine has passed through the bore of the stem portion of the funnel member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
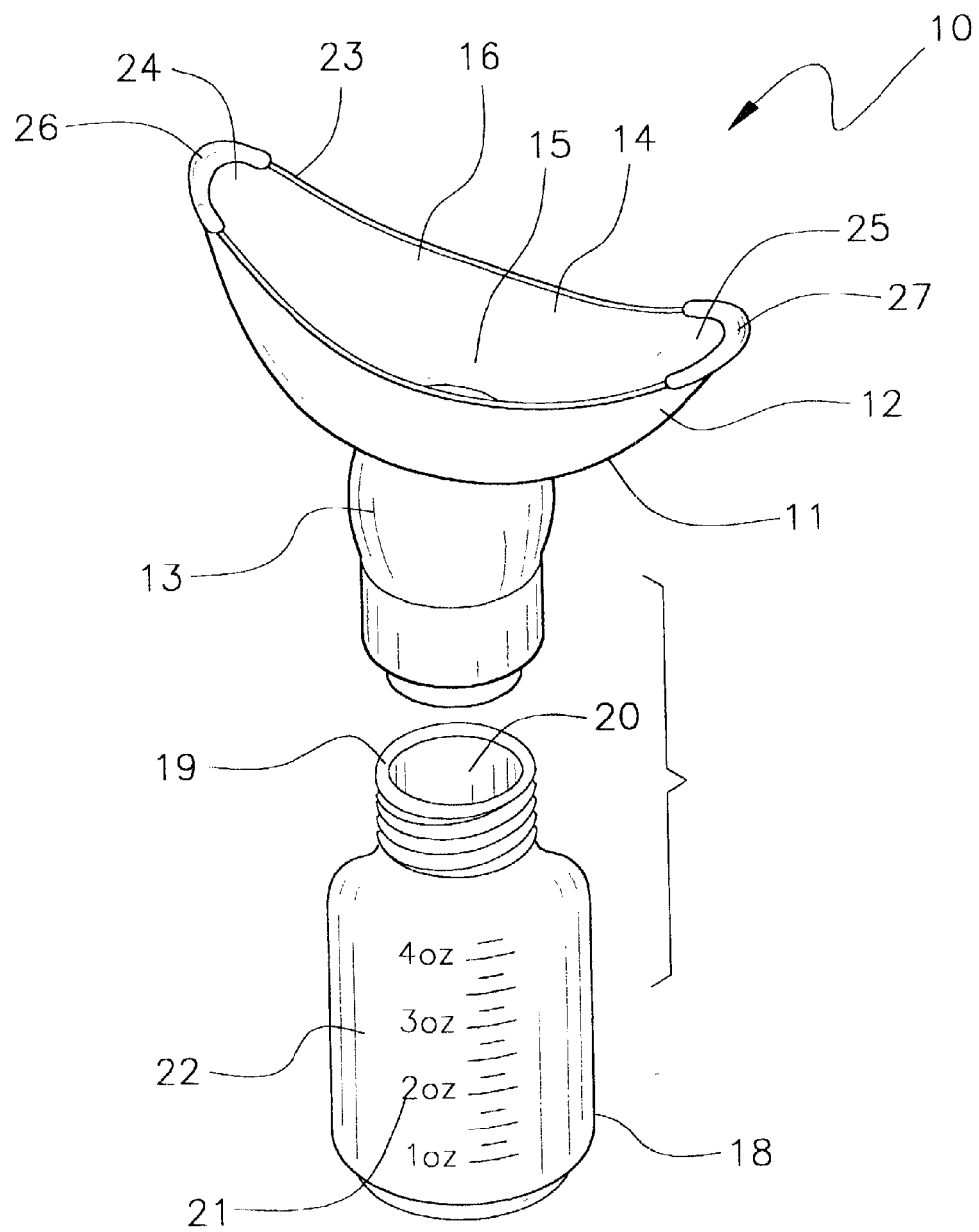
FIG. 1 is a perspective view of a new urine collection device according to the present invention.

With reference now to the drawings, and in particular to FIGS. 1 through 4 thereof, a new urine collection device embodying the principles and concepts of the present invention and generally designated by the reference numeral 10 will be described.

As best illustrated in FIGS. 1 through 4, the urine collection device 10 generally comprises a funnel member 11 having a bowl portion 12 and a stem portion 13. The bowl portion 12 has a perimeter wall 14 defining a cavity 15. The cavity 15 of the bowl portion 12 has an open top 16 whereby the open top 16 of the cavity 15 is designed for permitting urine to enter the cavity 15 of the bowl portion 12. The stem portion 13 has a bore 17. The bore 17 is in fluid communication with the cavity 15 of the bowl portion 12 whereby the bore 17 of the stem portion 13 is designed for permitting urine collected in the bowl portion 12 to pass through the stem portion 13.

A collection member 18 is selectively coupled to the stem portion 13 of the funnel member 11 opposite the bowl portion 12. The collection member 18 has a peripheral wall 19 defining an interior space 20. The interior space 20 of the collection member 18 is in fluid communication with the bore 17 of the stem portion 13 of the funnel member 11. The interior space 20 of the collection member 18 is designed for collecting and storing urine when the urine has passed through the bore 17 of the stem portion 13 of the funnel member 11.

The collection member 18 has indicia 21. The indicia 21 is positioned on an exterior surface 22 of the collection member 18. The indicia 21 is designed for indicating information needed for identifying the urine sample stored in the collection member 18.

The bowl portion 12 has an upper edge 23 forming an upper crest 24 and a lower crest 25. The bowl portion 12 is elongated whereby the bowl portion 12 is designed for being positioned between the legs of the user. The upper crest 24 is designed for being positioned along a front of a groin of the user for inhibiting urine from splashing out of a front of the bowl portion 12. The lower crest 25 is designed for being positioned along a rear of the groin of the user for inhibiting urine from splashing from a rear of the bowl portion 12.

A forward pad member 26 is coupled to the upper crest 24 of the bowl portion 12. The forward pad member 26 is for cushioning contact between the upper crest 24 and the user when the bowl portion 12 is positioned between the legs of the user. A rearward pad member 27 is coupled to the lower crest 25 of the bowl portion 12. The rearward pad member 27 is for cushioning contact between the lower crest 25 and the user when the bowl portion 12 of positioned between the legs of the user.

Figure 2:
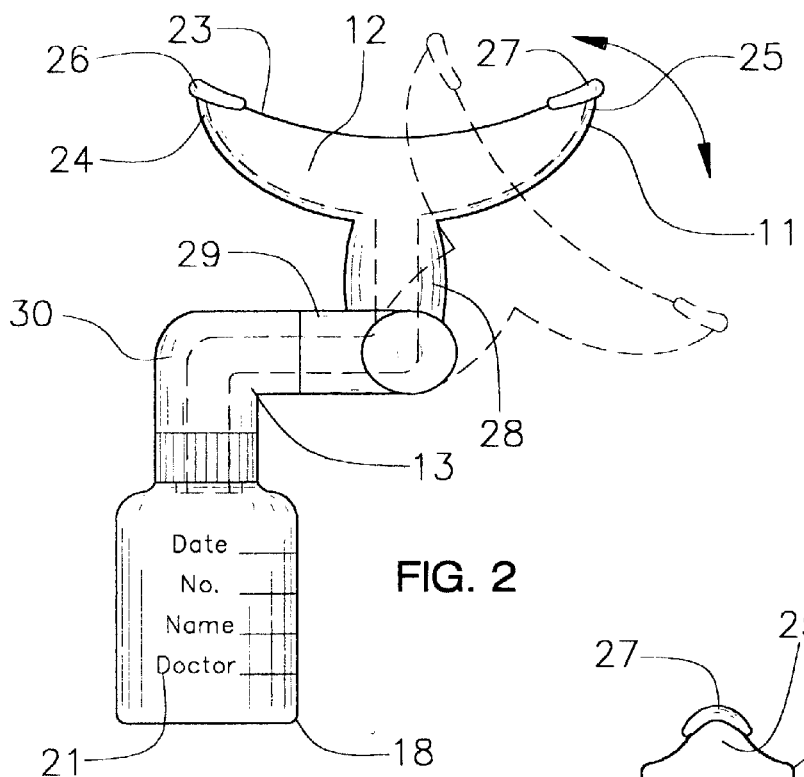
FIG. 2 is a side view of an alternate embodiment of the present invention.
Figure 3:
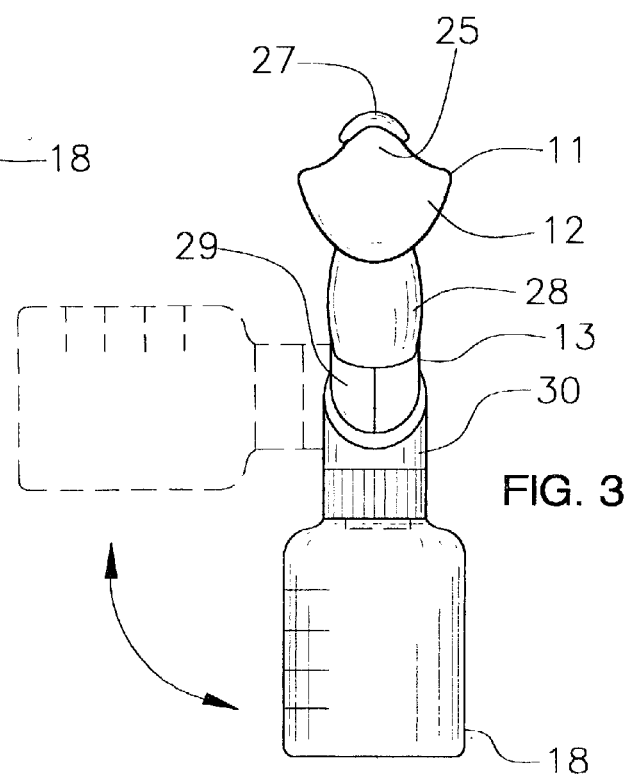
FIG. 3 is a front view of the alternate embodiment of the present invention shown in FIG. 2.
Figure 4:
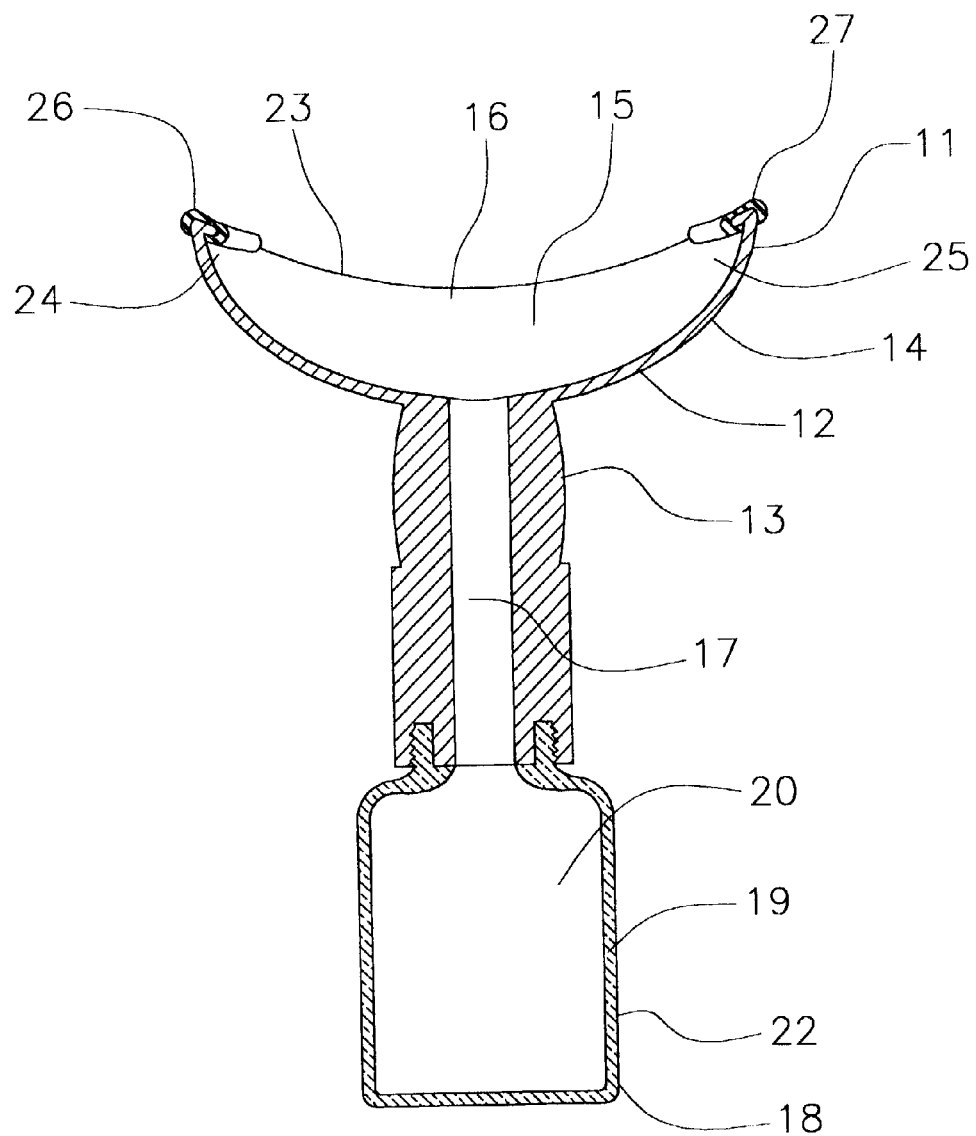
FIG. 4 is a cross-sectional view of the present invention in FIG. 1.

In an alternate embodiment, as shown in FIGS. 2 and 3, the stem portion 13 of the funnel member 11 has a first end portion 28 and a medial portion 29. The first portion end portion of the stem portion 13 is coupled to the bowl portion 12 of the funnel member 11. The first end portion 28 is pivotally coupled to the medial portion 29 of the stem portion 13. The bowl portion 12 is substantially pivotally positionable with respect to the medial portion 29 whereby the bowl portion 12 is designed for being positioned for comfort when the bowl portion 12 is positioned between the legs of the user. The stem portion 13 of the funnel member 11 has a second end portion 30. The second end of the stem portion 13 is rotatably coupled to the medial portion 29 opposite the first end portion 28. The second end of the of the stem portion 13 is selectively coupled to the collection member 18. The second end portion 30 of the stem portion 13 is for permitting the collection member 18 to be rotatably positioned around an axis of the medial portion 29 of the stem portion 13.

In use, the user couples the collection member 18 to the stem portion 13 of the funnel member 11. The bowl portion 12 of the funnel member 11 is then positioned between the legs of the user adjacent the groin of the user. The user then urinates into the bowl portion 12 and the urine is collected in the collection member 18. The collection member 18 is then given to medical personnel to be labeled and sent for testing.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A urine collection device for collecting urine from a user for medical analysis, the urine collection device comprising:

a funnel member having a bowl portion and a stem portion, said stem portion being integrally coupled to said bowl portion to inhibit leaking between said stem portion and said bowl portion, said bowl portion having a perimeter wall defining a cavity, said cavity of said bowl portion having an open top such that said open top of said cavity is adapted for permitting urine to enter said cavity of said bowl portion, said stem portion having a bore, said bore being in fluid communication with said cavity of said bowl portion such that said bore of said stem portion is adapted for permitting urine collected in said bowl portion to pass through said stem portion;

a collection member being selectively coupled to said stem portion of said funnel member opposite said bowl portion, said collection member having a peripheral wall defining an interior space, said interior space of said collection member being in fluid communication with said bore of said stem portion of said funnel member, said interior space of said collection member being adapted for collecting and storing urine when the urine has passed through said bore of said stem portion of said funnel member;

said stem portion of said funnel member having a first end portion and a medial portion, said first portion end portion of said stem portion being coupled to said bowl portion of said funnel member, said first end portion being pivotally coupled to said medial portion of said stem portion, said bowl portion being substantially pivotally positionable with respect to said medial portion such that said bowl portion is adapted for being positioned for comfort when said bowl portion is positioned between the legs of the user;

said stem portion of said funnel member having a second end portion, said second end of said stem portion being rotatably coupled to said medial portion opposite said first end portion, said second end of said of said stem portion being selectively coupled to said collection member, said second end portion of said stem portion being for permitting said collection member to be rotatably positioned around an axis of said medial portion of said stem portion.

2. The urine collection device as set forth in claim 1, further comprising:

said collection member having indicia, said indicia being positioned on an exterior surface of said collection member, said indicia being adapted for indicating information needed for identifying the urine sample stored in said collection member.

3. The urine collection device as set forth in claim 1, further comprising:

said bowl portion having an upper edge forming an upper crest and a lower crest, said bowl portion being elongated such that said bowl portion is adapted for being positioned between the legs of the user, said upper crest being adapted for being positioned along a front of a groin of the user for inhibiting urine from splashing out of a front of said bowl portion, said lower crest being adapted for being positioned along a rear of the groin of the user for inhibiting urine from splashing from a rear of said bowl portion.

4. The urine collection device as set forth in claim 3, further comprising:

a forward pad member being coupled to said upper crest of said bowl portion, said forward pad member being for cushioning contact between said upper crest and the front of the pelvis of the user when said bowl portion is positioned between the legs of the user.

5. The urine collection device as set forth in claim 3, further comprising:

a rearward pad member being coupled to said lower crest of said bowl portion, said rearward pad member being for cushioning contact between said lower crest and the rear of the pelvis of the user when said bowl portion is positioned between the legs of the user.

6. A urine collection device for collecting urine from a user for medical analysis, the urine collection device comprising:

a funnel member having a bowl portion and a stem portion, said bowl portion having a perimeter wall defining a cavity, said cavity of said bowl portion having an open top such that said open top of said cavity is adapted for permitting urine to enter said cavity of said bowl portion, said stem portion having a bore, said bore being in fluid communication with said cavity of said bowl portion such that said bore of said stem portion is adapted for permitting urine collected in said bowl portion to pass through said stem portion;

a collection member being selectively coupled to said stem portion of said funnel member opposite said bowl portion, said collection member having a peripheral wall defining an interior space, said interior space of said collection member being in fluid communication with said bore of said stem portion of said funnel member, said interior space of said collection member being adapted for collecting and storing urine when the urine has passed through said bore of said stem portion of said funnel member;

said stem portion of said funnel member having a first end portion and a medial portion, said first portion end portion of said stem portion being coupled to said bowl portion of said funnel member, said first end portion being pivotally coupled to said medial portion of said stem portion, said bowl portion being substantially pivotally positionable with respect to said medial portion such that said bowl portion is adapted for being positioned for comfort when said bowl portion is positioned between the legs of the user; and said stem portion of said funnel member having a second end portion, said second end of said stem portion being rotatably coupled to said medial portion opposite said first end portion, said second end of said of said stem portion being selectively coupled to said collection member, said second end portion of said stem portion being for permitting said collection member to be rotatably positioned around an axis of said medial portion of said stem portion.

7. The urine collection device as set forth in claim 6, further comprising:

said collection member having indicia, said indicia being positioned on an exterior surface of said collection member, said indicia being adapted for indicating information needed for identifying the urine sample stored in said collection member.

8. The urine collection device as set forth in claim 6, further comprising:

said bowl portion having an upper edge forming an upper crest and a lower crest, said bowl portion being elongated such that said bowl portion is adapted for being positioned between the legs of the user, said upper crest being adapted for being positioned along a front of a groin of the user for inhibiting urine from splashing out of a front of said bowl portion, said lower crest being adapted for being positioned along a rear of the groin of the user for inhibiting urine from splashing from a rear of said bowl portion.

9. The urine collection device as set forth in claim 8, further comprising:

a forward pad member being coupled to said upper crest of said bowl portion, said forward pad member being for cushioning contact between said upper crest and the user when said bowl portion is positioned between the legs of the user.

10. The urine collection device as set forth in claim 8, further comprising:

a rearward pad member being coupled to said lower crest of said bowl portion, said rearward pad member being for cushioning contact between said lower crest and the user when said bowl portion is positioned between the legs of the user.

11. A urine collection device for collecting urine from a user for medical analysis, the urine collection device comprising:

a funnel member having a bowl portion and a stem portion, said bowl portion having a perimeter wall defining a cavity, said cavity of said bowl portion having an open top such that said open top of said cavity is adapted for permitting urine to enter said cavity of said bowl portion, said stem portion having a bore, said bore being in fluid communication with said cavity of said bowl portion such that said bore of said stem portion is adapted for permitting urine collected in said bowl portion to pass through said stem portion;

a collection member being selectively coupled to said stem portion of said funnel member opposite said bowl portion, said collection member having a peripheral wall defining an interior space, said interior space of said collection member being in fluid communication with said bore of said stem portion of said funnel member, said interior space of said collection member being adapted for collecting and storing urine when the urine has passed through said bore of said stem portion of said funnel member;

said bowl portion having an upper edge forming an upper crest and a lower crest, said bowl portion being elongated such that said bowl portion is adapted for being positioned between the legs of the user, said upper crest being adapted for being positioned along a front of a groin of the user for inhibiting urine from splashing out of a front of said bowl portion, said lower crest being adapted for being positioned along a rear of the groin of the user for inhibiting urine from splashing from a rear of said bowl portion; and a forward pad member being coupled to said upper crest of said bowl portion, said forward pad member being for cushioning contact between said upper crest and the front of the pelvis of the user when said bowl portion is positioned between the legs of the user;

said stem portion of said funnel member having a first end portion and a medial portion, said first portion end portion of said stem portion being coupled to said bowl portion of said funnel member, said first end portion being pivotally coupled to said medial portion of said stem portion, said bowl portion being substantially pivotally positionable with respect to said medial portion such that said bowl portion is adapted for being positioned for comfort when said bowl portion is positioned between the legs of the user;

said stem portion of said funnel member having a second end portion, said second end of said stem portion being rotatably coupled to said medial portion opposite said first end portion, said second end of said of said stem portion being selectively coupled to said collection member, said second end portion of said stem portion being for permitting said collection member to be rotatable positioned around an axis of said medial portion of said stem portion.

12. The urine collection device as set forth in claim 11, further comprising:

said collection member having indicia, said indicia being positioned on an exterior surface of said collection member, said indicia being adapted for indicating information needed for identifying the urine sample stored in said collection member.

13. The urine collection device as set forth in claim 11, further comprising:

a rearward pad member being coupled to said lower crest of said bowl portion, said rearward pad member being for cushioning contact between said lower crest and the rear of pelvis of the user when said bowl portion is positioned between the legs of the user.

* * * * *